United States Patent
Hoshino

(10) Patent No.: US 9,107,638 B2
(45) Date of Patent: Aug. 18, 2015

(54) MEDICAL IMAGING SYSTEM

(71) Applicant: Konica Minolta, Inc., Chiyoda-ku, Tokyo (JP)

(72) Inventor: Yoshihide Hoshino, Hachioji (JP)

(73) Assignee: KONICA MINOLTA, INC. (JP)

(*) Notice: Subject to any disclaimer, the term of this patent is extended or adjusted under 35 U.S.C. 154(b) by 64 days.

(21) Appl. No.: 14/096,835

(22) Filed: Dec. 4, 2013

(65) Prior Publication Data
US 2014/0169522 A1    Jun. 19, 2014

(30) Foreign Application Priority Data

Dec. 18, 2012 (JP) .................. 2012-275216

(51) Int. Cl.
*A61B 6/00* (2006.01)
*G06T 7/00* (2006.01)

(52) U.S. Cl.
CPC .......... *A61B 6/484* (2013.01); *A61B 6/505* (2013.01); *A61B 6/5217* (2013.01); *G06T 7/0012* (2013.01); *G06T 7/0083* (2013.01); G06T 2207/10116 (2013.01); G06T 2207/20136 (2013.01); G06T 2207/30008 (2013.01)

(58) Field of Classification Search
CPC ...... A61B 6/484; A61B 6/505; A61B 6/5217; G06T 7/0012; G06T 7/0083; G06T 2207/10116; G06T 2207/20136; G06T 2207/30008
USPC .................. 378/36, 62, 70
See application file for complete search history.

(56) References Cited

U.S. PATENT DOCUMENTS

| | | | | |
|---|---|---|---|---|
| 7,889,838 B2* | 2/2011 | David et al. | | 378/36 |
| 2010/0119041 A1* | 5/2010 | Ohara | | 378/87 |
| 2010/0220832 A1* | 9/2010 | Ning et al. | | 378/4 |
| 2010/0290590 A1* | 11/2010 | Ouchi et al. | | 378/62 |

FOREIGN PATENT DOCUMENTS

| | | |
|---|---|---|
| JP | 2008-200359 A | 9/2008 |
| WO | 2011033798 A1 | 3/2011 |

OTHER PUBLICATIONS

A. Momose et al., Phase Tomography by X-ray Talbot Interferometry for Biological Imaging, J. Appl. Phys., vol. 45, 2006, pp. 5254-5262.
K. Hibino et al., Phase shifting for nonsinusoidal waveforms with phase-shift errors, J. Opt. Soc. Am. A, vol. 12, No. 4, Apr. 1995, pp. 761-768.

(Continued)

*Primary Examiner* — Irakli Kiknadze
(74) *Attorney, Agent, or Firm* — Cantor Colburn LLP

(57) ABSTRACT

A medical imaging system includes an X-ray imaging apparatus and an image processor. The X-ray imaging apparatus is provided with a Talbot or Talbot-Lau interferometer and includes an X-ray source, an X-ray detector, and a subject table. The image processor generates a differential phase image, and optionally, one or both of an X-ray absorption image and a small-angle scattering image of the subject on the basis of the image signal of the subject. The image processor specifies a location of an edge of a bone in the joint on the basis of at least one of the generated images; and detects an edge of a cartilage in the joint in the differential phase image on the basis of the specified location of the bone edge to quantitatively measure a feature of the cartilage.

6 Claims, 6 Drawing Sheets

(56) References Cited

OTHER PUBLICATIONS

M. Nagashima et al., Optimization of the joint and cartilage: diagnostic potential of the differential interferential contrast X-ray imaging, Proceedings of the 14th Japanese Research Society of Clinical Anatomy, Sep. 11, 2010. Japanese Research Society of Clinical Anatomy, Feb. 2011, No. 11, pp. 56-57, http://www.jrsca.jp/contents/records/contents/PDF/11-PDF/p56.pdf (accessed on Dec. 11, 2012), with English Abstract.

M. Takeda et al., Fourier-transform method of fringe-attern analysis for computer-based topography and interferometry, J. Opt. Soc. Am., vol. 72, No. 1, Jan. 1982, pp. 156-160.

W. Yashiro et al., Efficiency of capturing a phase image using cone-beam x-ray Talbot interferometry, J. Opt. Soc. Am. A, vol. 25, Aug. 2008, pp. 2025-2039.

\* cited by examiner

MEDICAL IMAGING SYSTEM

The present invention claims priority under 35 U.S.C. §119 to Japanese Application No. 2012-275216 filed Dec. 18, 2012, the entire content of which is incorporated herein by reference.

BACKGROUND OF THE INVENTION

1. Field of the Invention

The present invention relates to a medical imaging system including an X-ray imaging apparatus provided with a Talbot interferometer or Talbot-Lau interferometer.

2. Description of Related Art

It is quite difficult to capture X-ray absorption images (i.e., common X-ray images captured with traditional silver halide films) of patient's joint cartilage.

Magnetic resonance imaging (MRI), which can image joint cartilage, requires a high-cost apparatus and has high running costs and thus has increased inspection costs. Besides, MRI produces low resolution images that involve, for example, a risk of inaccurate measurement of the thickness of cartilage.

With MRI, a doctor specialized in imaging diagnostic estimates the thickness or other features of cartilage from captured images, on the basis of knowledge or experience, in many cases. A doctor, who is not specialized in imaging diagnostic, cannot determine the features from such low resolution images and has no choice but to relay on the specialist's estimation.

A conventional diagnosis of rheumatoid arthritis or osteoarthritis includes capturing an X-ray image (i.e., absorption image) of a joint such as a finger or knee joint. The doctor estimates the thickness, abrasion, or other states of the cartilage that is not visualized in the image, from the distance of a gap in the joint (i.e., the distance of a gap between two bones forming the joint) shown in the X-ray image.

The inventor of the present invention et al. have studied an X-ray imaging apparatus provided with a Talbot interferometer using the Talbot effect, which achieves imaging by sensing phase shifts in X-rays passing through an object, and an X-ray imaging apparatus provided with a Talbot-Lau interferometer which is an application of the Talbot interferometer (see Japanese Unexamined Patent Application Publication No. 2008-200359 and WO 2011/033798, for example). These interferometers are known to achieve imaging of mammary tissue and any other tissue which are not likely to appear on usual X-ray absorption images due to a small X-ray absorptive difference.

As described later, an X-ray imaging apparatus provided with a Talbot interferometer or Talbot-Lau interferometer is known to produce moire images which can be reconstructed into at least three types of images by a scheme using the principle of fringe scanning (see K. Hibino et al, J. Opt. Soc. Am. A, Vol. 12, (1995), pp. 761-768; and A. Momose et al, J. Appl. Phys., Vol. 45, (2006), pp. 5254-5262, for example) or by the Fourier transform (see M. Takeda et al, J. Opt. Soc. Am, Vol. 72, No. 1, (1982), p. 156, for example).

The three types of images consist of an absorption image (i.e., usual X-ray absorption image) reflecting the contrast produced by X-ray absorption, a differential phase image reflecting the contrast based on phase information, and a small-angle scattering image reflecting the contrast produced by small-angle scattering.

The inventor of the present invention et al. have applied such X-ray technology using a Talbot interferometer or Talbot-Lau interferometer to imaging of joint cartilage and found that an X-ray imaging apparatus provided with a Talbot interferometer or Talbot-Lau interferometer can produce at least differential phase images of cartilage in a cadaveric joint, as disclosed in Nagashima, Masabumi and seven others. "Optimization of Joint and Cartilage: Diagnostic Potential of Differential Interferential Contrast X-ray Imaging". Proceedings of the 14th Japanese Research Society of Clinical Anatomy, 2010-09-11. Japanese Research Society of Clinical Anatomy, February 2011, No. 11, pp. 56-57, http://www.jr-sca.jp/contents/records/contents/PDF/11-PDF/p5_6.pdf (accessed on Dec. 11, 2012).

As described later, an improved X-ray imaging apparatus provided with a Talbot interferometer or Talbot-Lau interferometer successfully captures a moire image of a joint in a living body instead of a cadaveric joint and reconstructs the image to produce at least a differential phase image of joint cartilage.

This technology allows the thickness or other features of cartilage to be accurately measured from a reconstructed image, and thus provides a medical imaging system which allows quantitative measurement of the thickness or other features of cartilage.

SUMMARY OF THE INVENTION

An object of the present invention, which has been made to solve such a problem, is to provide a medical imaging system that can accurately measure the thickness or other quantitative features of joint cartilage from, for example, a differential phase image of the cartilage reconstructed from a moire image captured by an X-ray imaging apparatus provided with a Talbot interferometer or Talbot-Lau interferometer.

According to an aspect of a preferred embodiment of the present invention, there is provided an medical imaging system including: an X-ray imaging apparatus provided with a Talbot interferometer or a Talbot-Lau interferometer, the X-ray imaging apparatus including: an X-ray source which emits X-rays, an X-ray detector including conversion elements to generate an electrical signal according to the emitted X-rays, and reading the electrical signal generated by the conversion elements, as an image signal, and a subject table to hold a subject for a joint of the subject to be imaged; and an image processor which generates a differential phase image of the subject and optionally generates one of or both of an X-ray absorption image and a small-angle scattering image of the subject on the basis of the image signal of the subject imaged by the X-ray imaging apparatus, wherein the image processor specifies a location of an edge of a bone in the joint on the basis of at least one of the differential phase image, the X-ray absorption image, and the small-angle scattering image; and detects an edge of a cartilage in the joint in the differential phase image on the basis of the specified location of the edge of the bone to quantitatively measure a feature of the cartilage in the joint.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein.

DESCRIPTION OF THE PREFERRED EMBODIMENTS

Embodiments of a medical imaging system according to the present invention will now be described with reference to the attached drawings.

[Structure of Medical Imaging System]

As described above, a medical imaging system according to the invention includes an X-ray imaging apparatus provided with a Talbot interferometer or Talbot-Lau interferometer.

The Talbot effect, which is the principle of a Talbot interferometer etc., refers to a phenomenon in which when coherent light passes through a first grating (G1 grating) with slits at regular distances, the image of the grating is formed at regular distances along the direction of the propagating light (see Japanese Unexamined Patent Application Publication No. 2008-200359, for example). The formed images are called self images. The Talbot interferometer has a second grating (G2 grating) at the location of a self image, and forms moire fringes by slightly shifting the second grating.

Positioning an object in front of the first grating disrupts the moire fringes. A medical imaging system including an X-ray imaging apparatus provided with a Talbot interferometer captures images including moire fringes (hereinafter referred to as moire images) acquired through irradiation with coherent X-rays with and without a subject positioned in front of the first grating. The system then analyzes these images to produce a reconstructed image of the subject.

Talbot-Lau interferometers are also known which have a multi-slit grating (G0 grating) between the X-ray source and the first grating (see WO 2011/033798, for example). A medical imaging system including an X-ray imaging apparatus provided with a Talbot-Lau interferometer basically has a similar structure to a system provided with a Talbot interferometer except that it contains a multi-slit grating to use a high-output incoherent X-ray source which can increase radiation dose per unit time, for example.

As described above, an X-ray imaging apparatus provided with a Talbot interferometer or Talbot-Lau interferometer, which captures moire images, can produce at least three types of reconstructed images: an X-ray absorption image, a differential phase image, and a small-angle scattering image, by capturing moire images with a scheme based on the principle of fringe scanning or by analyzing the moire images with Fourier transform.

Figure 1:
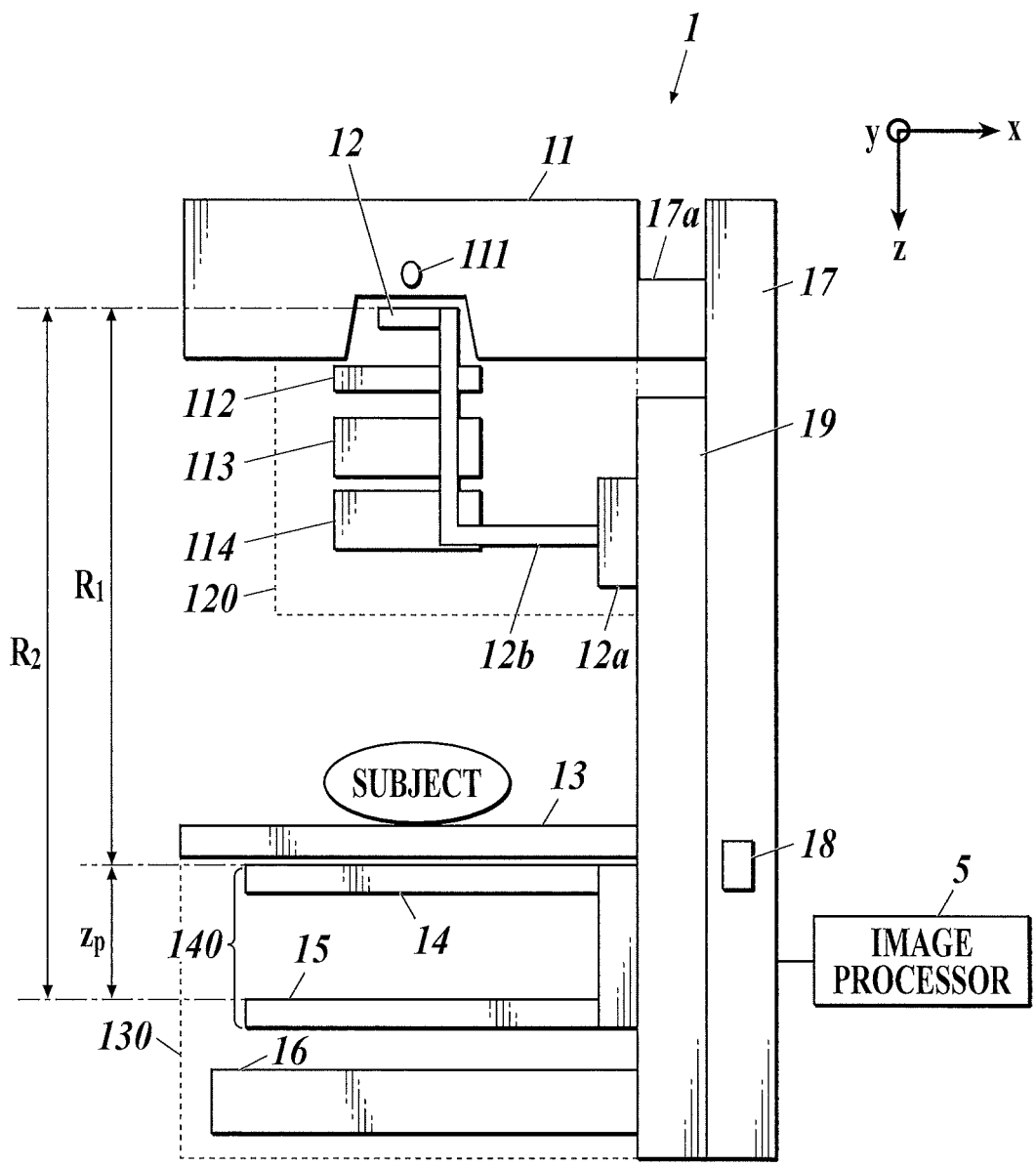
FIG. 1 is a schematic view of an X-ray imaging system according to an embodiment of the present invention.

The structure of the medical imaging system according to this embodiment will now be briefly described. FIG. 1 schematically illustrates the medical imaging system of this embodiment.

As shown in FIG. 1, the medical imaging system includes an X-ray imaging apparatus 1 and an image processor 5. In FIG. 1, the X-ray imaging apparatus 1 is provided with a Talbot-Lau interferometer. In the following description, the X-ray imaging apparatus 1 is provided with the Talbot-Lau interferometer. The invention is also applicable to an X-ray imaging apparatus provided with a Talbot interferometer. The following description is also applicable to an X-ray imaging apparatus provided with a Talbot interferometer.

The image processor 5 generates reconstructed images, i.e., an X-ray absorption image, a differential phase image, and a small-angle scattering image of the subject from a moire image produced by the X-ray imaging apparatus 1. As described later, the image processor 5 does not necessarily have to generate all of the absorption image, differential phase image, and small-angle scattering image. The image processor 5 generates at least the differential phase image among the three types of images, on the basis of the image signals (i.e., the moire image) of the subject imaged by the X-ray imaging apparatus 1. The process in the image processor 5 will be described later in detail.

[Structure of X-ray Imaging Apparatus]

As shown in FIG. 1, the X-ray imaging apparatus 1 includes an X-ray source 11; a first covering unit 120 containing a multi-slit 12; a second covering unit 130 containing a subject table 13, a first grating 14, a second grating 15, and an X-ray detector 16; a support 17; a main body 18; and a base 19.

The X-ray imaging apparatus 1 in FIG. 1 is upright. The X-ray source 11 (having a focal point 111), the multi-slit 12, the subject table 13, the first grating 14, the second grating 15, and the X-ray detector 16 are disposed in sequence in the z direction, i.e., the direction of the gravity. The z-direction is the direction of illumination axis of X rays emitted from the X-ray source 11.

In FIG. 1, the first covering unit 120 contains an adjuster 12a, a mounting arm 12b, an additional filter 112, an irradiation field diaphragm 113, and an irradiation field lamp 114. The second covering unit 130 contains a grating assembly 140 including the first grating 14 and the second grating 15.

In this embodiment, the components in the first and second covering units 120 and 130 are each protected with a covering material (not shown). In the X-ray imaging apparatus 1 capturing moire images by fringe scanning, the second covering unit 130 is provided with a mechanism (not shown) for moving the second grating 15 in a given direction (the x direction in FIGS. 1 and 2), for example.

The adjuster 12a is used for fine adjustment of the location of the multi-slit 12 along the x, y, and z directions and the rotational angle of the multi-slit 12 around the x, y, and z axes. The adjuster 12a is not essential if the multi-slit 12 can be accurately fixed to the support 19. In FIG. 1, the reference numeral 17a is a cushion connecting the X-ray source 11 and the support 17.

Figure 2:
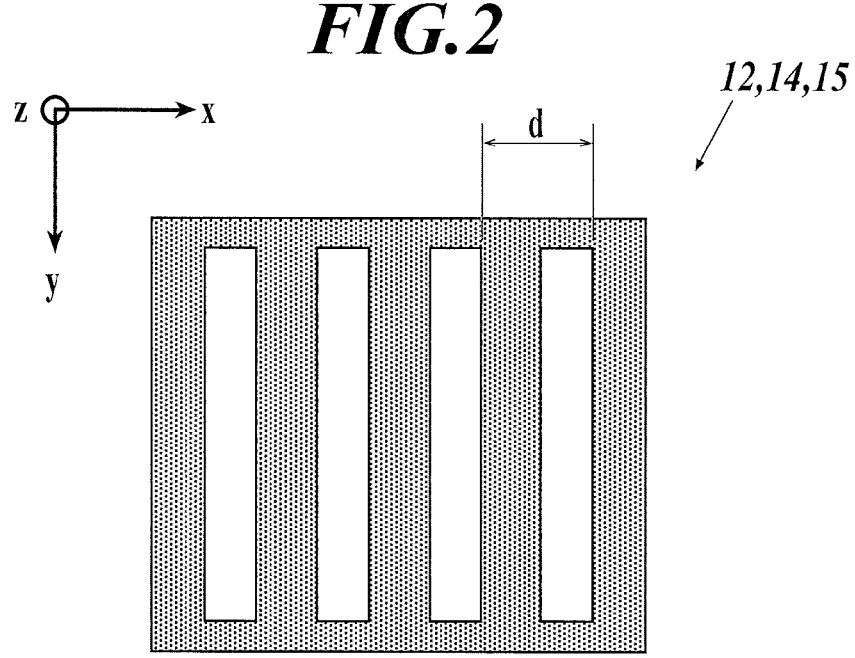
FIG. 2 is a schematic plan view of a multi-slit, a first grating, and a second grating.

As illustrated in FIG. 2, the multi-slit 12 (G0 grating), the first grating 14 (G1 grating), and the second grating 15 (G2 grating) are diffraction gratings provided with plural slits arranged in the x direction orthogonal to the z direction, i.e., the direction of the illumination axis of X-rays. Refer to, for example, WO 2011/033798 for the material or process for forming these gratings.

As shown in FIG. 2, the multi-slit 12, the first grating 14, and the second grating 15 have inter-slit distances d ($d_0$, $d_1$, and $d_2$, respectively). As shown in FIG. 1, $R_1$ is the distance between the multi-slit 12 and the first grating 14, $R_2$ is the distance between the multi-slit 12 and the second grating 15, and $z_p$ is the distance between the first-grating 14 and the second grating 15. Expressions (1) to (4) or similar conditions hold (see W. Yashiro et al., Efficiency of capturing a phase image using cone-beam X-ray Talbot interferometry. Opt. Soc. Am., 25, 2025, 2008).

$$z_p = pd_1 \cdot \alpha d_2/\lambda \quad (1)$$

$$d_2 = R_2 d_1/(R_1 \alpha) \quad (2)$$

$$R_1/d_0 = z_p/d_2 \quad (3)$$

$$1/d_0 = \alpha/d_1 - 1/d_2 \quad (4)$$

Here, p and α are Talbot order and Talbot constant, respectively, which vary depending on the type of the first grating 14. Typical examples are listed below. In this table, n is a positive integer.

TABLE 1

| | π/2 SHIFT DIFFRACTION GRATING | π SHIFT DIFFRACTION GRATING | ABSORPTION DIFFRACTION GRATING |
|---|---|---|---|
| p | (2n − 1)/2 | (2n − 1)/8 | n |
| α | 1 | 2 | 1 |

Under the above conditions, self images formed by X-rays passing through the slits of the multi-slit 12 and the first grating 14 can be superimposed on each other on the second grating 15.

[Principles of Talbot Interferometer and Talbot-Lau Interferometer]

Figure 3:
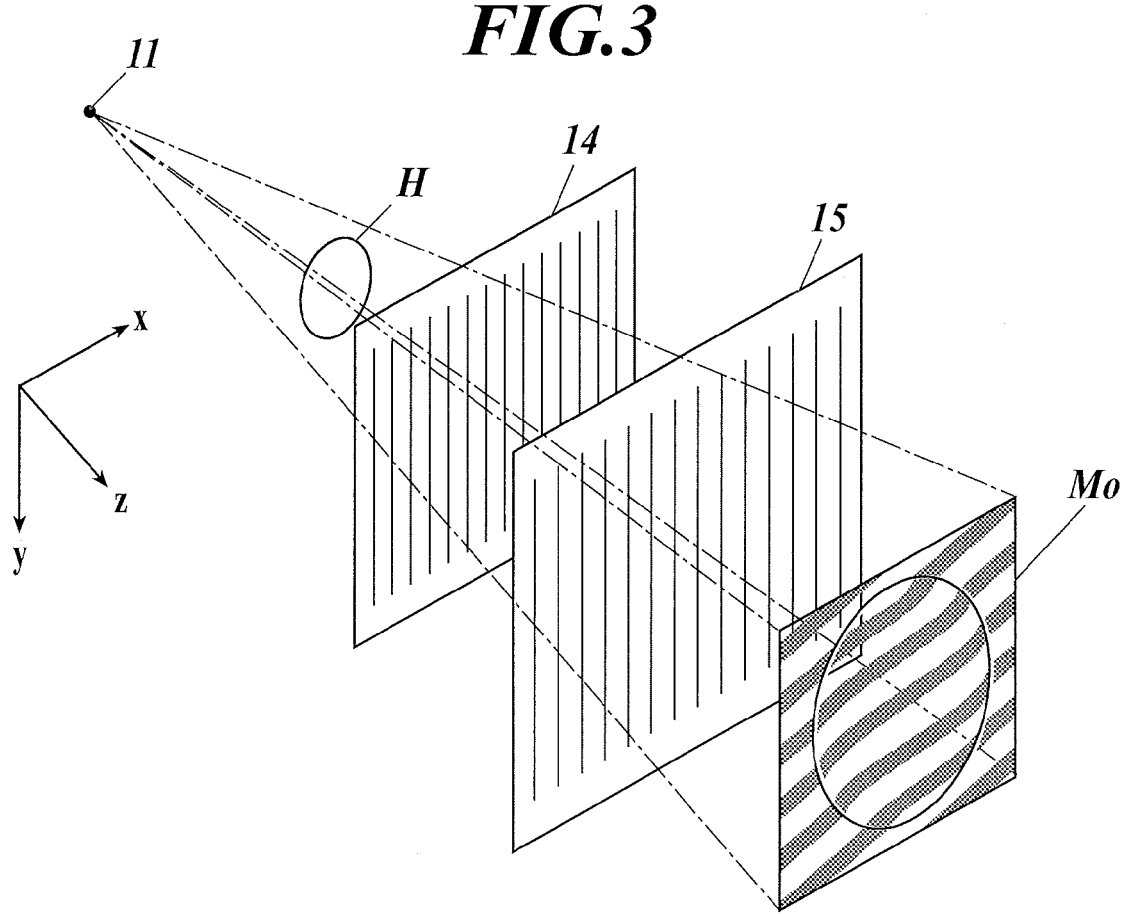
FIG. 3 illustrates the principles of a Talbot interferometer.

The Principle common to Talbot interferometer and Talbot-Lau interferometer will now be described. As shown in FIG. 3, when X-rays from the X-ray source 11 pass through the first grating 14, the X-rays produce images formed at regular distances along the z direction. These images are called self images. Such a phenomenon in which self images are formed at regular distances along the z direction is called Talbot effect.

The second grating 15 is located at the position where a self image formed by the first grating 14 appears. In addition, a direction in which the slits of the second grating 15 extend (i.e., the y direction in FIG. 2) is slightly shifted from the direction in which the slits of the first grating 14 extend. Thus, a moire image (shown as Mo in FIG. 3) appears on the second grating 15.

FIG. 3 depicts moire image Mo as being away from the second grating 15 to avoid any confusion which may be caused by depicting moire image Mo on the second grating 15. In practice, moire image Mo is formed on and downstream of the second grating 15. In FIG. 3, the subject H present between the X-ray source 11 and the first grating 14 is reflected in the moire image Mo. If the subject H is not present, only moire fringes appear, as described later.

The subject H present between the X-ray source 11 and the first grating 14 may shift the phase of X-rays, depending on the type of the subject. Thus, as shown in FIG. 3, the fringes in the moire image are disturbed around the frame of the subject. The disturbed moire fringes are detected through processing of the moire image. The image of the subject is then reconstructed. This is the principle of the Talbot interferometer.

[Other Structures in X-ray Imaging Apparatus]

Other structures in FIG. 1 will now be described. The subject table 13 holds the subject during imaging of a joint or joints of the subject. The X-ray detector 16 includes a two-dimensional array of conversion elements (not shown) to generate electrical signals according to emitted X-rays and reads the electrical signals generated by the conversion elements, as image signals.

As the distance between the X-ray detector 16 and the second grating 15 increases, blurring of a moire image captured by the X-ray detector 16 increases. To avoid such a phenomenon, the X-ray detector 16 is preferably fixed to the support 19 so as to be in contact with the second grating 15.

The X-ray detector 16 is a flat panel detector (FPD), for example. The FPD may be of an indirect type that converts X-rays into electrical signals through scintillator with photoelectric elements or of a direct type that directly converts X-rays into electrical signals. The X-ray detector 16 may be any FPD or any other image capturing unit such as a charge coupled device (CCD) or an X-ray camera.

The main body 18 is connected to the X-ray source 11, the X-ray detector 16, and other components and controls irradiation with X-rays from the X-ray source 11. The main body 18 transmits a moire image generated by the X-ray detector 16 to the image processor 5. Alternatively, the main body 18 generates a moire image from electrical signals read by the X-ray detector 16 and transmits the moire image to the image processor 5.

In addition, the main body 18 comprehensively controls the X-ray imaging apparatus 1. Not surprisingly, the main body 18 may contain any appropriate unit or device, such as an input unit, a display unit, or a storage unit.

[Structure and Other Details of Image Processor]

The structure and operation of the image processor 5 in the medical imaging system according to this embodiment will now be described. The operation of the medical imaging system according to this embodiment will also be described.

In this embodiment, as described above, the image processor 5 is configured to generate the reconstructed images, i.e., the X-ray absorption image, differential phase image, and small-angle scattering image of the subject from a moire image produced by the X-ray imaging apparatus 1. The image processor does not necessarily have to generate all these three reconstructed images but may generate at least a differential phase image (i.e., the X-ray absorption image and the small-angle scattering image are optional).

In this embodiment, the image processor 5 is a computer with a bus connected to a central processing unit (CPU), a read only memory (ROM), a random access memory (RAM), an input/output interface, and other components, which are not shown in the drawing. The X-ray imaging apparatus 1 and the image processor 5 are connected via a network.

In response to reception of multiple moire images captured by fringe scanning in the X-ray imaging apparatus 1 provided with a Talbot interferometer or Talbot-Lau interferometer, the image processor 5 reconstructs an X-ray absorption image, a differential phase image, and a small-angle scattering image from the moire images.

An approach for imaging in the X-ray imaging apparatus 1 without fringe scanning include increasing the angle between the direction in which the slits of the first grating 14 extend and the direction in which the slits of the second grating 15 extend, transmitting a moire image with finer moire fringes from the X-ray imaging apparatus 1 to the image processor 5, and analyzing the moire image in the image processor 5 by Fourier transform. The approach allows an X-ray absorption image, a differential phase image, and a small-angle scattering image to be generated in a similar manner to the above-stated case.

Figure 4:
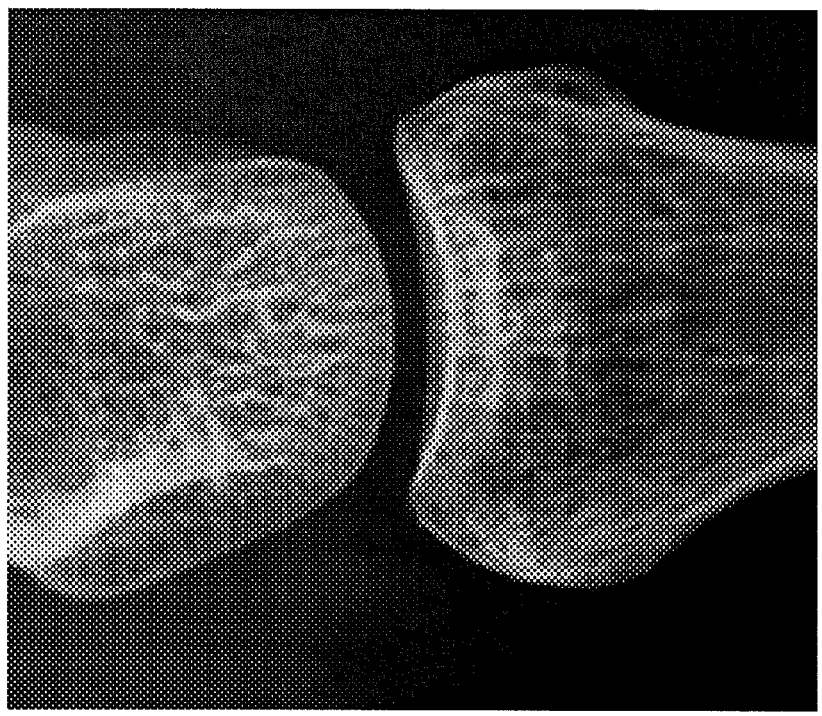
FIG. 4 is an example X-ray absorption image (photograph) of a joint.
Figure 5:
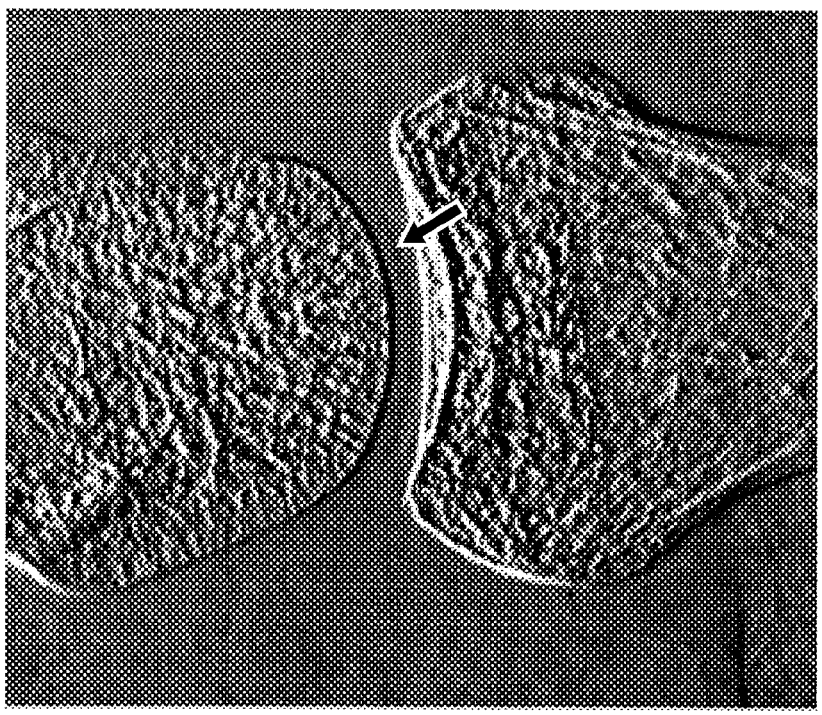
FIG. 5 is an example differential phase image (photograph) of the joint showing an edge of joint cartilage.

The resulting images are shown in shown in FIG. 4 or FIG. 5, for example. Note that FIGS. 4 and 5 are the exemplary absorption image and differential phase image, respectively, of patient's hand joints, which are generated from the same moire image (a group of moire images if without fringe scanning).

The studies conducted by the inventor of the present invention et al. have found that, as indicated by the arrow in FIG. 5, a joint cartilage appears in a differential phase image reconstructed from moire images captured by the X-ray imaging apparatus 1 provided with a Talbot interferometer or Talbot-Lau interferometer. In FIG. 5, the edge of the joint cartilage appear as a streak between two bones forming the joint.

As described above, the studies conducted by the inventor of the present invention et al. have found that such a medical imaging system allows a target joint of the patient to appear in an image without incision for exposing the joint. In particular, the joint is placed on the subject table 13 of the X-ray imaging apparatus 1 provided with a Talbot interferometer or Talbot-Lau interferometer to be irradiated with X-rays for imaging. The resulting moire image (s) is reconstructed into a differential phase image of cartilage in the joint.

The image processor 5 measures the thickness or other features of joint cartilage from the differential phase image of the cartilage. An approach will now be described to detect the edges of the cartilage from a differential phase image (see FIG. 5) for the purpose of measuring the thickness or other features of the cartilage.

[Approach to Detect Edges of Cartilage from Differential Phase Image]

In this embodiment, in order to detect the location or other features of joint cartilage from a differential phase image, the image processor 5 first specifies the locations of the edges of the bones in the joint in an X-ray absorption image, a differential phase image, and/or a small-angle scattering image.

As described above, joint cartilage itself is hard to capture in an X-ray absorption image. In contrast, the edges of the bones in the joint clearly appear in any of an absorption image as shown in FIG. 4, a differential phase image as shown in FIG. 5, and a small-angle scattering image (not shown). The analysis of any of these images can specify the locations of the edges of the bones in the joint.

An example process will now be explained of specifying the locations of the edges of the bones in the joint by image analysis. It should be understood that the invention can employ any process which can specify the locations of the edges of the bones from an image, in addition to that explained below.

For instance, the process includes calculation of a difference between the signal values of a target pixel and each of the horizontally adjacent pixels in the X-ray absorption image of FIG. 4. If the absolute value of the difference is greater than or equal to a predetermined threshold, then the target pixel is marked. Similarly, the pixels on the right and left of the target pixel are processed in sequence as next target pixels.

Such a process is performed on every pixel row of the absorption image. In addition, such a process may be performed only on a predetermined area of the absorption image (i.e., an area at and around the center of the image in which the joint is captured). After the process, the absorption image has multiple marked pixels.

As a result, a pixel array passing through the vertical and horizontal center of the absorption image has at least two marked pixels. For instance, in FIG. 4, these marked pixels correspond to the edges of the right and left bones. Other marked pixels may be present in the pixel array.

Figure 6:
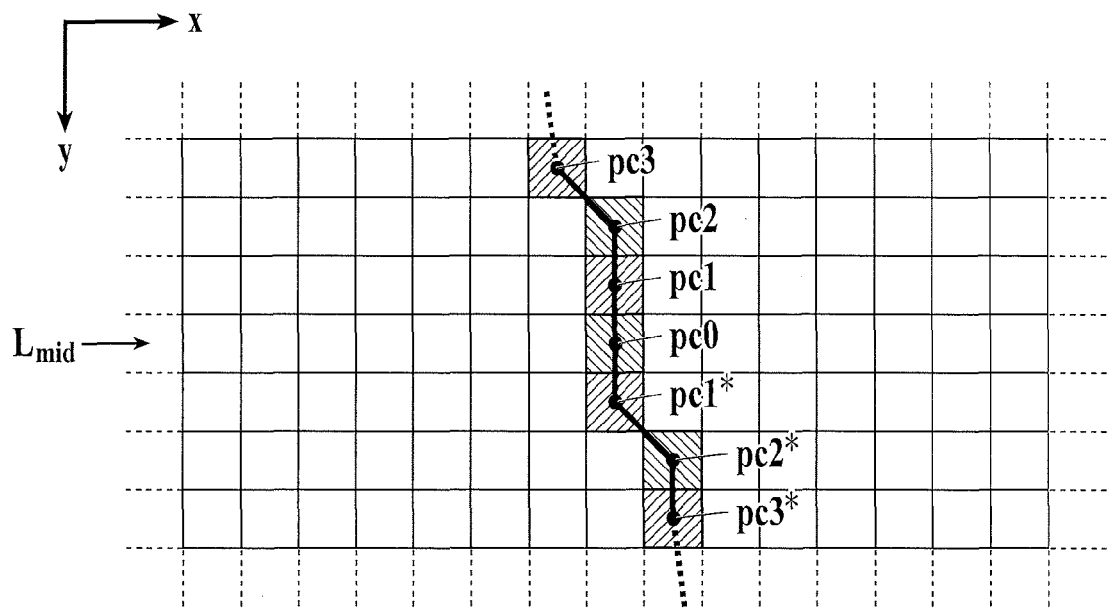
FIG. 6 illustrates a series of marked pixels corresponding to the location of an edge of a bone specified from a differential phase image etc.

Then, as illustrated in FIG. 6, the process goes to search of a predetermined area above and below a marked pixel pc0 present in a pixel row Lmid passing through the vertical and horizontal center of the absorption image. If other marked pixels pc1 and pc1* are found, the first-found marked pixel pc0 and the newly-found marked pixels pc1 and pc1* are linked.

Similarly, predetermined areas are then searched for marked pixels pc1 and pc1*. If other marked pixels pc2 and pc2* are found, marked pixels pc1 and pc2 are linked and marked pixels pc1* and pc2* are linked. Such a process is performed on each pixel row in the entire area or a predetermined area of an absorption image in the vertical direction. Thus, as shown in FIG. 6, several groups of linked marked pixels are detected in the image.

As shown in the absorption image of FIG. 4 and the differential phase image of FIG. 5, the opposed edges of the two bones forming the joint have substantially arc-shaped cross sections (visually identifiable shapes in the image). In other words, the joint cannot be bent smoothly if the edges of the bones in the joint do not have arc-shaped cross sections.

For every group detected in the above manner, the linked marked pixels are subjected to curve fitting. The group forming a shape closest to an arc is regarded as a group of pixels corresponding to an edge of a bone in the joint.

The image processor 5 first specifies groups of pixels corresponding to the edges of the bones in the joint from an X-ray absorption image, a differential phase image, or a small-angle scattering image in the above-described manner, for example. Thus, the locations of the edges of the bones in the joint can be specified from the image.

As shown in FIGS. 4 and 5, the edges of the two bones face each other in the joint. For this reason, to specify the locations of the edges of the bones in the joint in the above-described manner, two groups forming arc shapes facing each other are preferably identified as groups representing the locations of the edges of the two bones in the joint.

In some cases, three or more groups of marked pixels forming arc shapes are detected from the image. In such cases, two groups facing each other can be extracted and identified as the edges of the bones in the above-described manner, for example. Thus, optimization of conditions that should be satisfied by the detected groups can improve the accuracy of specifying a group of pixels corresponding to the edges of the bones in the joint.

The locations of the edges of the bones in the joint may be specified from one of an absorption image, a differential phase image, and a small-angle scattering image. Alternatively, the locations of the edges of the bones in the joint may be specified from two or more of these images. In that case, a match or mismatch between the locations specified from images may be detected to improve the accuracy of specifying the locations of the edges of the bones in the joint.

The image processor 5 then detects the location of the edge of the joint cartilage. As described above, joint cartilage is hard to capture in an X-ray absorption image. However, the X-ray imaging apparatus 1 in the medical imaging system of this embodiment can capture the joint cartilage at least in a differential phase image, as shown in FIG. 5.

The image processor 5 specifies the locations of the edges of the bones in the joint from the image(s) in the above-described manner, and then applies the locations to the differential phase image. If a differential phase image is used for the process of specifying the locations of the edges of the bones in the joint, the resulting location information (i.e., information on the coordinates of the pixels in the differential phase image corresponding to the edges of the bones) is used in the following process without any change.

The locations of the edges of the bones in the joint in a captured image are common among the X-ray absorption image, the differential phase image, and the small-angle scattering image which are generated from the same moire image as described above. Thus, even if an absorption image or a small-angle scattering image is used for the process of specifying the locations of the edges of the bones in the joint, the resulting location information (i.e., information on the coordinates of the pixels) can be converted into location information for a differential phase image for use in the following process.

The image processor 5 then detects the location of the edge of the joint cartilage, on the basis of the location of the edge of a bone in the joint specified from the differential phase image.

As indicated by the arrow in FIG. 5, a differential phase image based on a moire image captured by the medical imaging system according to this embodiment contains the edge of joint cartilage that appears as a streak between two bones forming the joint. In this embodiment, the location of the edge of cartilage is detected by identifying the streak in the joint in the differential phase image.

The streak in the image has larger signal values than the adjacent pixels. Thus, a difference (or its absolute value) between the signal values of adjacent pixels may be evaluated to specify the location of the streak. This can detect the location of the edge of cartilage.

Figure 7:
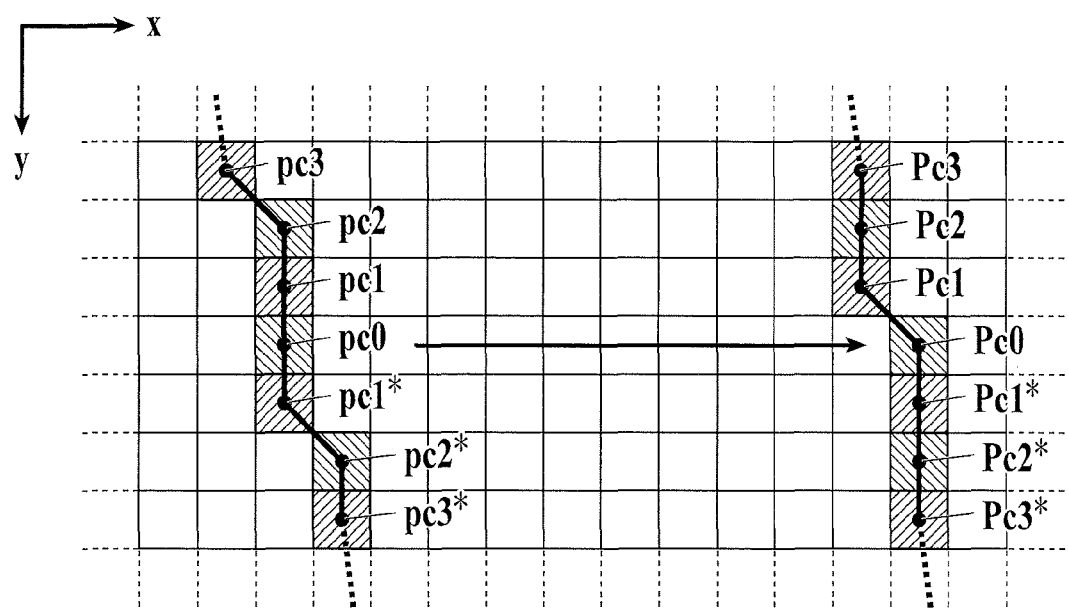
FIG. 7 illustrates a series of marked pixels corresponding to the location of the edge of the bone in the differential phase image and pixels corresponding to the edge of the cartilage.

In particular, as illustrated in FIG. 7, a difference is calculated between the signal value of a pixel in the specified location of the edge of the bone and the signal value of each of the horizontally adjacent pixels. If the absolute value of the difference is greater than or equal to a predetermined threshold, then the pixel is determined as representing a portion of the locations of the edges of the cartilage.

In such a case, as described above, if two groups corresponding to the edges of the bones facing each other are specified in the joint, the process proceeds from one group to the other group, the one group projecting toward the other group. For instance, in FIG. 5, the calculation of the absolute value of the difference between the signal values of adjacent pixels proceeds from the group corresponding to the left bone to the group corresponding to the right bone.

As shown in FIG. 5, the specified locations of the edges of the bones and the adjacent area contain portions with very low signal values (e.g., the left bone in FIG. 5) and very high signal values (e.g., the right bone in FIG. 5) in some cases. This process may incorrectly determine the edges of the portions as the edges of the cartilage. To avoid such a misinterpretation, pixels with very high and low signal values in and around the specified edges of the bones are preferably removed from the list of candidates to undergo the process.

As shown in FIG. 5, the streak in the differential phase image representing the edges of the cartilage appears as a portion slightly darker than the dark background. It should therefore be understood that the threshold is set to such a value that ensures accurate detection of even a small difference in the darkness.

For instance, a process based on the differential phase image of FIG. 5 outputs the result shown in FIG. 7 in which a group of pixels Pc0, Pc1, Pc2, . . . and Pc1*, Pc2*, . . . representing the edge of the cartilage appears on the right side of a group of marked pixels pc0, pc1, pc2, . . . and pc1*, pc2*, . . . representing the edge of the identified bone.

In this embodiment, as described above, the image processor 5 specifies the edge of the bone in the joint (marked pixels pc0, pct, pc2, . . . and pc1*, pc2*, . . . ) from an X-ray absorption image, a differential phase image, and/or a small-angle scattering image, and then detects the edge of the joint cartilage (Pc0, Pct, Pc2, . . . and Pc1*, Pc2*, . . . ) on the basis of the edge of the bone from the differential phase image.

[Quantitative Measurement of Features of Cartilage]

Quantitative measurement will now be explained of the features of the joint cartilage, which is carried out in the image processor 5 of the medical imaging system according to this embodiment on the basis of the information on the detected cartilage. Such features will also be exemplified to help the explanation.

The following accurate quantitative measurement of the features of cartilage allows, for example, the doctor to check the degree of abrasion or damage to the cartilage or to quantitatively check progression of such abrasion or damage by comparison with prior data. This improves the procedure for the affected part and allows for appropriate determination, for example, of transition to a stronger medication.

EXAMPLE 1

Examples of the quantitatively measured features of joint cartilage include the distance R (see FIG. 8) between the edge A of the detected cartilage and the edge B of the bone in the joint specified in the differential phase image as described above.

If the location at which the distance R is measured in the joint varies at every imaging, continuous monitoring of changes in distance R cannot be achieved, preventing the observation of the degree of abrasion and other abrasion states of cartilage. The location at which the distance R is measured can be kept at a given location in the joint in the following manner, for example.

As described above, if the cross section of the edge B of the bone in the joint does not have an arc-shaped edge, the joint cannot be bent smoothly. The cross section therefore partly has a substantially arc-shape edge in many cases. For this reason, a portion that can be relatively accurately approximated by an arc shape (the shaded portion in the drawing) is specified in the joint in FIG. 8, for example.

For instance, the center C of curvature of the arc, by which the portion is approximated, is calculated in a differential phase image to quantitatively measure the distance R between the bone edge B and the cartilage edge A which lies along a line L connecting the center C and the center of the portion.

Thus, regardless of variations among images in the orientation of the joint placed on the subject table 13 in FIG. 1 (i.e., the direction from one bone to the other bone), the portion of the joint which can be relatively accurately approximated by an arc shape barely varies among imaging operations, allowing the distance R, i.e., the thickness of the cartilage, to be measured at substantially the same location in the cartilage at every imaging.

In such a case, the distance R is calculated as a distance between pixels lying on the line L. In particular, in FIG. 7, when the line L (not shown in FIG. 7) passes through, for example, marked pixels pc1 and Pc2, the pixel count (the number of pixels) that corresponds to the distance between the marked pixels pc1 and Pc2 is calculated.

If the coordinates of the marked pixels pc1 and Pc2 in a differential phase image are, for example, (x1,y1) and (X2, Y2), respectively, the distance Rp in pixel count is represented by:

$$Rp=\{(x1-X2)^2+(y1-Y2)^2\}^{1/2} \quad (5).$$

The distance Rp represented by such a pixel count may be converted into the actual distance R, on the basis of the enlargement factor of the differential phase image and the pixel size of the X-ray imaging apparatus 1.

This configuration enables accurate quantitative measurement of a feature of the joint cartilage, i.e., the distance R of the cartilage at the center of an arc-shaped portion (i.e., the thickness of the cartilage in the area corresponding to the portion), which is particularly prone to abrasion. For instance, the continuous monitoring of the distance R in the area corresponding to the portion allows for accurate observation of the abrasion, the degree of abrasion, and other abrasion states of the cartilage.

[Modification 1]

Although not shown in the drawing, the image processor 5 in Example 1 may include a display unit to display images, and input unit, such as a keyboard and a mouse, through which an operator, for example, a radiological technologist inputs instructions. The display unit shows a differential phase image, a line L, and the like. For instance, the distance R (i.e., the thickness) of cartilage on the line L input by the operator via the input unit may be calculated.

EXAMPLE 2

Instead of or in addition to the calculation of only one distance R of the cartilage in the area corresponding to the portion (i.e., distance R of the cartilage at the center of an arc-shaped portion, which is particularly prone to abrasion) as in Example 1, the process may calculate at least one of the maximum Rmax, the minimum Rmin, the difference ΔR between the maximum and the minimum, and the average Rave of the distance R at least in the area corresponding to a portion of the joint which can be approximated by an arc shape.

Figure 8:
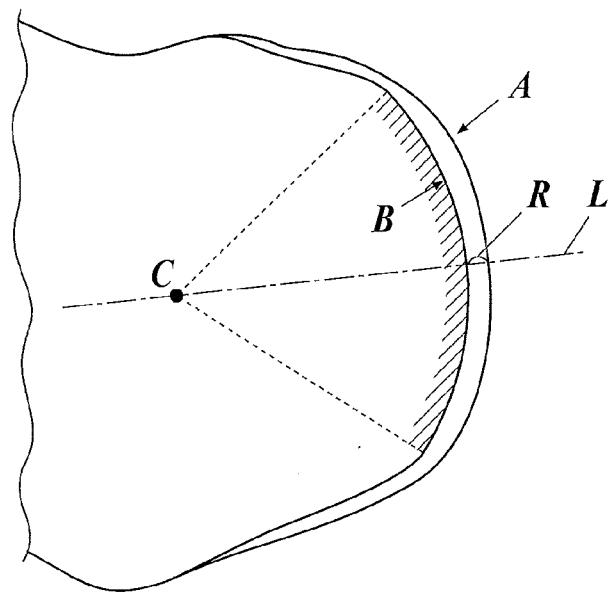
FIG. 8 illustrates an edge of joint cartilage, an edge of a bone, the distance between these edges, and the center of curvature etc.

For instance, in FIG. 8, the line L is rotated about the center C within the range corresponding to the portion that can be approximated by an arc shape (the shaded portion in the drawing). While the line L is being rotated, the distance R (i.e., thickness) of the cartilage is calculated in the above-described manner. The maximum Rmax, the minimum Rmin, the difference ΔR between the maximum and the minimum, and/or the average Rave of the distance R are determined on the basis of the calculated distance R.

A target area for the calculation of the maximum Rmax etc. of the distance R may be wider than the area corresponding to the portion that can be approximated by an arc shape.

This configuration enables accurate quantitative measurement of a feature of the joint cartilage, i.e., the distance R (thickness) of the cartilage for a wider target are; and enables accurate quantitative measurement of the maximum Rmax and the minimum Rmin etc. This enables detailed checking of these values. The continuous monitoring of the distance R in the target area allows for detailed and accurate observation of whether abrasion has occurred and of the degree of abrasion, and other abrasion states of the cartilage.

[Modification 2]

With the same configuration as Modification 1, the operator may specify the area in which the distance R (i.e., thickness) of the cartilage is to be calculated, via the input unit. The maximum Rmax and the minimum Rmin etc. of the distance R in the cartilage may be then calculated in the specified area.

EXAMPLE 3

Instead of or in addition to the operations in Example 1 or 2, the cross-sectional area S of the cartilage may be measured.

For instance, the process starts with determination of the number of pixels (pixel count) lying between a marked pixel pc corresponding to the bone edge B and a marked pixel Pc corresponding to the cartilage edge A in FIG. 7, and then sums the pixel counts of all the pixel rows to determine the cross-sectional area Sp in pixel count. The cross-sectional area Sp represented by pixel count may be converted into an actual cross-sectional area S, on the basis of the enlargement factor of the differential phase image and the pixel size of the X-ray imaging apparatus 1.

This configuration enables accurate quantitative determination of a feature of the joint cartilage, i.e., the cross-sectional area S of the cartilage. For instance, the continuous monitoring of the cross-sectional area S of the cartilage allows for detailed and accurate observation of whether abrasion has occurred and of the degree of abrasion, and other abrasion states of the cartilage.

[Modification 3]

Figure 9A:
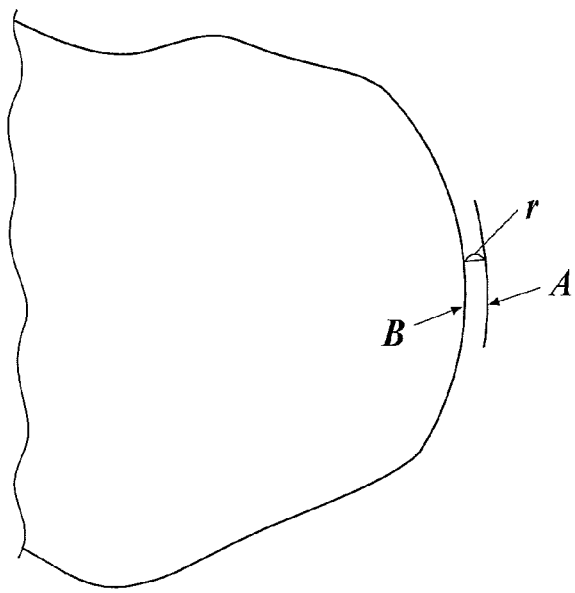
FIG. 9A illustrates the case in which a differential phase image includes only a part of the edge of the cartilage.

As shown in FIG. 9A, not all but only a part of the cartilage edge A is captured in the differential phase image in some cases in Examples 1 to 3.

In such a case, the process may include calculation of the distance r between the joint cartilage edge A (i.e., a part of the cartilage edge A) and the corresponding edge B of the bone in the joint identified in the differential phase image, selection of one of the predetermined cartilage shape models which matches the calculated distance r, and application of the selected shape model to the bone edge B. This procedure can estimate the shape of the cartilage edge A, which is not found in the differential phase image.

In particular, various patterns on the location or state of cartilage abrasion, which varies among different joints, are prepared on the basis of the prior data or other information. Thus, shape models for healthy cartilage (i.e., cartilage without abrasion), for cartilage with early-stage abrasion, for cartilage with severe abrasion, and for other states of cartilage are predetermined.

Figure 9B:
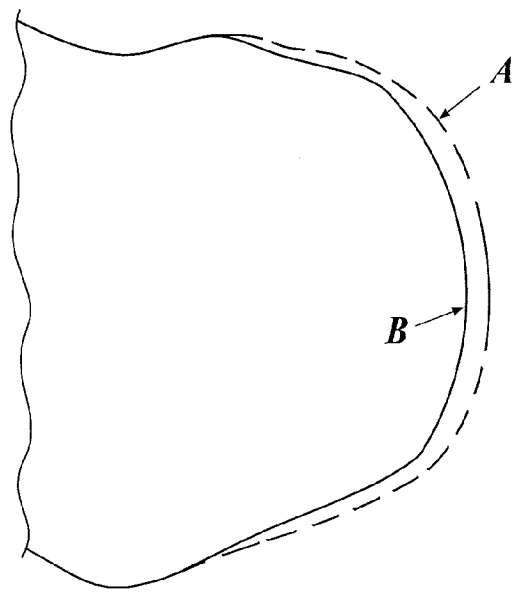
FIG. 9B illustrates the shape of the edge of the cartilage estimated by applying a shape model to the edge of the bone.

The process proceeds to the selection of one of the predetermined cartilage shape models that matches the distance r in the detected cartilage. If the distance r does not match any shape model, an additional shape model is created through interpolation between two shape models, for example, and then applied to the differential phase image. As shown in FIG. 9B, this procedure can estimate the shape of the cartilage edge A, which is not found in the differential phase image.

In that case, the shape model is prepared for every target site. Different shape models are preferably prepared depending on sex or age (adults or children), for example. Thus, an appropriate shape model is selected from a category satisfying the target site or sex etc. of a subject (patient).

EXAMPLE 4

Instead of or in addition to the operations in Examples 1 to 3, the length W of the joint cartilage edge A may be measured. The length W of the joint cartilage edge A is, for example, the full length from the top to the bottom of the cartilage edge A in FIG. 8.

An example procedure for measuring the length W of the joint cartilage edge A is as follows. The full length of a line connecting the centers of the pixels Pc representing the cartilage edge A (see FIG. 7) is calculated in pixel count. The resulting value is converted into an actual length W, on the basis of the enlargement factor of the differential phase image and the pixel size of the X-ray imaging apparatus 1.

Another example procedure for measuring the length W of the joint cartilage edge A is as follows. The total number of the pixels Pc0, Pc1, Pc2 . . . and Pc1*, Pc2* . . . representing the cartilage edge A is calculated. This value is converted into a length W, on the basis of the enlargement factor of the differential phase image and the pixel size of the X-ray imaging apparatus 1.

This configuration enables accurate quantitative measurement of a feature of the joint cartilage, i.e., the length W of the cartilage edge A. With progression of abrasion of the cartilage, the length W of the cartilage edge A decreases. For instance, the continuous monitoring of the length W of the cartilage edge A allows for detailed and accurate observation of whether abrasion has occurred and of the degree of abrasion, and other abrasion states of the cartilage.

[Modifications 1-4]

Future technology may allow damaged portions, e.g. chipped or cracked portions of cartilage to be clearly imaged. Unfortunately, current medical imaging systems cannot perform such clear imaging of a chipped or cracked portion as shown in, for example, FIG. 10 in which the edge A is not imaged at a damaged portion, e.g. a chipped or cracked portion of the cartilage (i.e., the portion indicated by D in the drawing).

Damage such as chipping or cracking of cartilage does not refer to thinning of entire cartilage due to abrasion or other factors, but represents partial thinning of cartilage due to chipping or cracking.

For instance, in Example 4, the length W of the edge A of cartilage with a damaged, e.g., chipped or cracked portion is significantly smaller than that at a normal state. Thus, Example 4 can achieve accurate detection of damage, e.g., chipping or cracking of cartilage.

Figure 10:
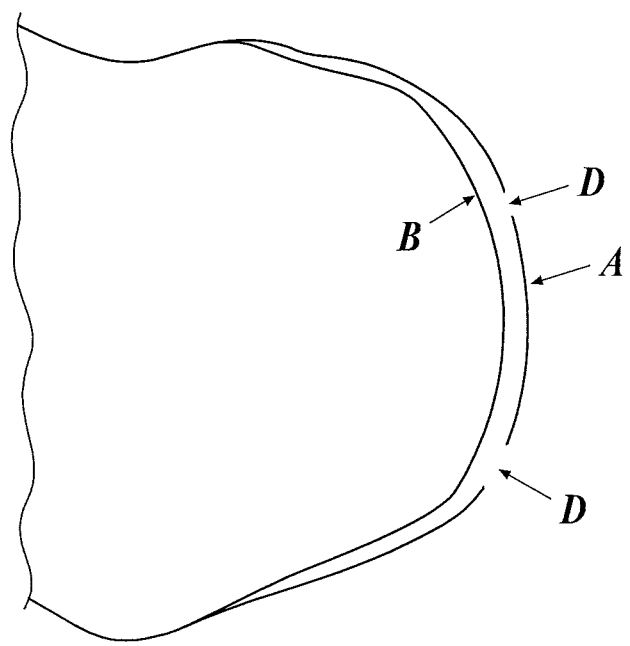
FIG. 10 illustrates the fact that the edge of the cartilage is not imaged at a chipping or cracking portion.

Damage such as chipping or cracking of cartilage appears as a non-imaged portion D in the cartilage edge A as illustrated in FIG. 10. In such a case, the cartilage edge A cannot be detected even in a step of detecting the cartilage edge A from the differential phase image on the basis of the specified joint bone edge B (see FIG. 7).

In other words, in a process of detecting the cartilage edge A in the differential phase image, a sequence of pixel rows where the cartilage edge A is not detected (see the portion D in FIG. 10) may indicate the damage, e.g., chipping or cracking of the cartilage.

Accordingly, in a differential phase image displayed on the screen (not shown) of the image processor 5, the portion D in which the cartilage edge A is not detected (i.e., in which the cartilage may be damaged) may be colored with a particular color or tagged with characters or voice.

The possibly damaged portion D in the cartilage (i.e., where the cartilage edge A is not detected) may be continuously monitored to find the increase in the area of the portion D.

[Advantageous Effects]

As described above, in a medical imaging system including an X-ray imaging apparatus 1 provided with a Talbot interferometer or Talbot-Lau interferometer according to this embodiment, the image processor 5 specifies the location of the edge B of the bone in the joint on the basis of at least one of an X-ray absorption image, a differential phase image, and a small-angle scattering image; and detects the cartilage edge A in the differential phase image on the basis of the specified location of the bone edge B. The features of the cartilage are then quantitatively measured, i.e., converted into numeric data, on the basis of the detected joint cartilage edge A and the like.

As described above, the inventor of the present invention et al. have found that joint cartilage can be captured in a differential phase image reconstructed from a moire image captured by the X-ray imaging apparatus 1 provided with a Talbot interferometer or Talbot-Lau interferometer. The X-ray absorption image, the differential phase image, and the small-angle scattering image can clearly show the bone in the joint, resulting in accurate determination of the location of the edge B of the bone.

The inventor of the present invention et al. have also found that the joint cartilage edge A in the differential phase image can be accurately detected on the basis of the specified location of the edge B of the bone in the joint. A medical imaging system according to this embodiment enables such accurate detection of the cartilage edge A, leading to accurate measurement of the features of the cartilage such as the distance R (i.e., the thickness of the cartilage) between the bone edge B and the cartilage edge A.

As mentioned above, a doctor specialized in imaging diagnostic has conventionally estimated the thickness or other features of cartilage from a low resolution image captured by MRI, on the basis of knowledge or experience, which does not always result in accurate measurement of the quantitative features of cartilage. By contrast, a medical imaging system of this embodiment allows the features of cartilage to be measured in the above-described manner and thus to be readily and accurately measured in a quantitative manner independent of human knowledge or experience.

Such accurate quantitative measurement of the features of cartilage allows, for example, the doctor to check the degree of abrasion or damage to the cartilage or to quantitatively check progression of such abrasion or damage by comparison with prior data. This improves the procedure for the affected part and allows for appropriate determination, for example, of transition to a stronger medication.

In this embodiment, the case in which a joint is formed simply by two facing bones is described, as illustrated in FIGS. 4 and 5, for example. This embodiment also allows the cartilage edge A to be detected on the basis of the edge B of the bone of a joint having a more complex structure.

It should be understood that the present invention is not limited to the above embodiment and various modifications can be made without departing from the spirit of the invention. For example, another type of phase image may be used instead of the differential phase image.

The entire disclosure of Japanese Patent Application No. 2012-275216 filed on Dec. 18, 2012 including description, claims, drawings, and abstract are incorporated herein by reference in its entirety.

Although various exemplary embodiments have been shown and described, the invention is not limited to the embodiments shown. Therefore, the scope of the invention is intended to be limited solely by the scope of the claims that follow.

What is claimed is:

1. A medical imaging system comprising:
an X-ray imaging apparatus provided with a Talbot interferometer or a Talbot-Lau interferometer, the X-ray imaging apparatus including:
an X-ray source which emits X-rays,
an X-ray detector including conversion elements to generate an electrical signal according to the emitted X-rays, and reading the electrical signal generated by the conversion elements, as an image signal, and a subject table to hold a subject for a joint of the subject to be imaged; and an image processor which generates a differential phase image of the subject and optionally generates one of or both of an X-ray absorption image and a small-angle scattering image of the subject on the basis of the image signal of the subject imaged by the X-ray imaging apparatus, wherein the image processor specifies a location of an edge of a bone in the joint on the basis of at least one of the differential phase image, the X-ray absorption image, and the small-angle scattering image; and detects an edge of a cartilage in the joint in the differential phase image on the basis of the specified location of the edge of the bone to quantitatively measure a feature of the cartilage in the joint.

2. The medical imaging system according to claim 1, wherein the image processor estimates a shape of the cartilage on the basis of information on a distance between the specified edge of the bone in the joint in the differential phase image and the edge of the cartilage in the joint detected in the differential phase image.

3. The medical imaging system according to claim 1, wherein the image processor measures the feature of the cartilage in the joint by calculating a distance between the edge of the bone in the joint and the edge of the cartilage in the joint in the differential phase image on the basis of an enlargement factor and a pixel size of the X-ray imaging apparatus.

4. The medical imaging system according to claim 3, wherein the image processor measures the feature of the cartilage in the joint by calculating at least one of a maximum of the distance in an area corresponding to a portion of the joint, a minimum of the distance in the area, a difference between the maximum and the minimum, and an average of the distance in the area.

5. The medical imaging system according to claim 1, wherein the image processor measures the feature of the cartilage in the joint by calculating a cross-sectional area of the cartilage on the basis of an enlargement factor and a pixel size of the X-ray imaging apparatus, the cross-sectional area corresponding to an area of a region surrounded by the edge of the bone in the joint and the edge of the cartilage in the joint in the differential phase image.

6. The medical imaging system according to claim 1, wherein the image processor measures the feature of the cartilage in the joint by calculating a length of the edge of the cartilage in the joint in the differential phase image on the basis of an enlargement factor and a pixel size of the X-ray imaging apparatus.

* * * * *